US011859928B2

(12) United States Patent
Koplin

(10) Patent No.: US 11,859,928 B2
(45) Date of Patent: Jan. 2, 2024

(54) SYSTEMS AND METHODS FOR FIREARM SAFETY

(71) Applicant: Humanistic Robotics, Inc., Bristol, PA (US)

(72) Inventor: Joshua K. Koplin, Bristol, PA (US)

(73) Assignee: Humanistic Robotics, Inc., Bristol, PA (US)

( * ) Notice: Subject to any disclaimer, the term of this patent is extended or adjusted under 35 U.S.C. 154(b) by 875 days.

(21) Appl. No.: 16/899,194

(22) Filed: Jun. 11, 2020

(65) Prior Publication Data

US 2021/0389069 A1 Dec. 16, 2021

(51) Int. Cl.
| | |
|---|---|
| *F41A 17/06* | (2006.01) |
| *G06K 19/07* | (2006.01) |
| *E05B 73/00* | (2006.01) |
| *A61B 5/024* | (2006.01) |
| *A61B 5/00* | (2006.01) |
| *A61B 5/08* | (2006.01) |
| *H04N 5/77* | (2006.01) |
| *G16H 40/67* | (2018.01) |
| *G16H 50/30* | (2018.01) |
| *H04N 23/51* | (2023.01) |

(52) U.S. Cl.
CPC ............ *F41A 17/063* (2013.01); *A61B 5/024* (2013.01); *A61B 5/08* (2013.01); *A61B 5/7455* (2013.01); *E05B 73/00* (2013.01); *G06K 19/0723* (2013.01); *G16H 40/67* (2018.01); *G16H 50/30* (2018.01); *H04N 5/772* (2013.01); *H04N 23/51* (2023.01)

(58) Field of Classification Search
CPC ...... F41A 17/46; F41A 17/063; F41A 17/066; F41A 17/06; F41A 17/00; F41A 17/30; F41A 17/04
USPC ................... 42/70.06, 70.07, 70.11, 70.01
See application file for complete search history.

(56) References Cited

U.S. PATENT DOCUMENTS

| | | | | |
|---|---|---|---|---|
| 8,819,979 | B2 * | 9/2014 | Kelly | ............ F41A 17/54 42/70.07 |
| 10,527,378 | B1 * | 1/2020 | Christian | ............ F41A 17/54 |
| 2020/0132404 | A1 * | 4/2020 | Adam Kemp | ............ F41A 17/54 |

FOREIGN PATENT DOCUMENTS

WO WO-03106794 A1 * 12/2003 ........... E05B 67/365

* cited by examiner

*Primary Examiner* — Reginald S Tillman, Jr.
(74) *Attorney, Agent, or Firm* — Meunier Carlin & Curfman LLC

(57) ABSTRACT

A modular system for preventing the unauthorized use of a firearm is provided. The system includes a safety module that is configured to attach to a firearm using a standard rail mount found on most firearms. The safety module includes a trigger bar that is configured to extend from the safety module to behind or through the side of the trigger of the firearm. The safety module further includes a locking mechanism that, in a first state, prevents the trigger bar from moving rearward and thereby also prevents the trigger from being pulled. The locking mechanism further includes a second state where the trigger bar is allowed to move with the trigger thereby allowing the trigger to be pulled.

20 Claims, 9 Drawing Sheets

*190*

*190*

*190*

SYSTEMS AND METHODS FOR FIREARM SAFETY

BACKGROUND

Firearm safety is an important issue worldwide. One aspect of firearm safety is the prevention of unauthorized firearm usage. One way to prevent unauthorized firearm usage is through the use of so-called smart guns. A smart gun is a type of firearm that is designed to only fire after an operator has been authenticated. Example methods for authentication include biometric authentication.

However, there are drawbacks associated with smart guns. First, there are estimated to be over a billion non-smart firearms in circulation world-wide. The existence of smart guns does nothing to prevent the unauthorized usage of existing non-smart firearms. Second, there are many styles and types of firearms, and each firearm owner has their own specific firearm preferences. Given the limited availability of smart guns, it is unlikely that every firearm owner will be able to find a smart gun that meets all of their specific preferences.

SUMMARY

A modular system for preventing the unauthorized use of a firearm is provided. The system includes a safety module that is configured to attach to a firearm using a standard rail mount found on most firearms. The safety module includes a trigger bar that is configured to extend from the safety module to behind of through the side of the trigger of the firearm. The safety module further includes a locking mechanism that, in a first state, prevents the trigger bar from moving rearward and thereby also prevents the trigger from being pulled. The locking mechanism further includes a second state where the trigger bar is allowed to move rearward with the trigger thereby allowing the trigger to be pulled and the weapon to fire.

The safety module may transition the locking mechanism between the first state and the second state based on the receipt of a code from an authorized user. In some embodiments, the safety module may include an RFID receiver that is configured to receive a code from a nearby RFID transmitter. The RFID transmitter may be part of a bracelet, ring, badge or other user device that may be worn by a designated user. When the RFID transmitter is near the RFID receiver, the RFID receiver may cause the RFID transmitter to emit a code associated with the user. The safety module may receive the code and may determine if the code matches one or more stored codes associated with authorized users. If so, the safety module may place the locking mechanism in the second state thereby allowing the trigger bar to move and the firearm to be fired. Else, the safety module may place the locking mechanism in the first state thereby preventing the trigger bar from moving and the firearm from firing. Additional features of the safety module are described further below.

The safety module as described herein provides many advantages over the prior art. First, because the safety module may attach to the rail system found on many firearms, the safety module may be used to provide smart safety features to existing firearms. Second, because the safety module includes a removeable and customizable trigger bar, the safety module can be adapted to fit a wide variety of gun sizes and shapes.

In one embodiment, a system for preventing the unauthorized use of a firearm is provided. The system may include: a housing that is removably attached to an exterior of a firearm; a locking mechanism within the housing; a trigger bar that is connected to the locking mechanism and that extends from the locking mechanism to a trigger of the firearm when the housing is attached to the firearm; and a processing component that is configured to place the locking mechanism in one of a first state or a second state, wherein in the first state the locking mechanism prevents the trigger bar from moving such that a normal movement of the trigger is impeded and in the second state the locking mechanism allows the trigger bar to move such that the normal movement of the trigger is unimpeded.

Embodiments may include some or all of the following features. The trigger bar may extend from the locking mechanism to behind the trigger. The processing component may be further configured to: wirelessly receive a code; determine if the received code is associated with an authorized user; and when it is determined that the received code is associated with an authorized user, place the locking mechanism in the second state. The processing component may be further configured to: wirelessly receive a code; determine if the received code is associated with an authorized user; and when it is determined that the received code is not associated with an authorized user, place the locking mechanism in the first state. Determining if the received code is associated with an authorized user may include the processing component: accessing one or more authorized user codes stored by the processing component in a memory; and determining if the received code matches any of the one or more authorized user codes.

The processing component may be further configured to: receive an instruction related to the one or more authorized user codes; and update the one or more authorized user codes in response to the received instruction. The instruction may be one or more of an instruction to add an authorized user code to the one or more authorized user codes, an instruction to remove an authorized user code from the one or more authorized user codes, and an instruction to make no changes to the one or more authorized user codes.

The processing component may be further configured to: determine that a threshold amount of time has passed since an instruction related to the one or more authorized user codes has been received; and in response to the determination, prevent the locking mechanism from being placed in the second state. The processing component may be further configured to: while in the second state: determine that a threshold amount of time has passed since a code has been received; and in response to the determination, place the locking mechanism in the first state.

The system may further include one or more sensors within the housing, wherein the one or more sensors are configured to collect data about the firearm and an operator of the firearm, and the processing component may be further configured to transmit the collected data to a server. The one or more sensors may include one or more of a camera or an accelerometer. The system may further include a camera within the housing, and the processor is further configured to: while in the second state, receive and store video data from the camera. The processing component may be further configured to: process the stored video data to determine an accuracy for an operator of the firearm.

The processing component may be further configured to: while in the second state: determine a number of rounds fired by the firearm; determine that the number of rounds exceeds a threshold number of rounds; and in response to the determination, place the locking mechanism in the first state.

The processing component may be further configured to determine the number of rounds using an accelerometer.

The processing component may be further configured to: wirelessly receive a first code and a second code; determine that the received first code and the received second code are both associated with an authorized user of a plurality of authorized users; and in response to the determination, place the locking mechanism in the second state. The first code may be associated with an operator of the firearm and the second code may be received from a non-operator of the firearm.

The processing component may be further configured to: determine a physiological state of an operator of the firearm; and based on the determined physiological state, place the locking mechanism in the first state or the second state. The processing component may be further configured to: provide haptic feedback based on the physiological state of the operator of the firearm. The physiological state is one or more of a breathing state or a heartbeat state.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described within a cloud-based contact center, it will become evident to those skilled in the art that the implementations are not limited thereto.

Figure 1:
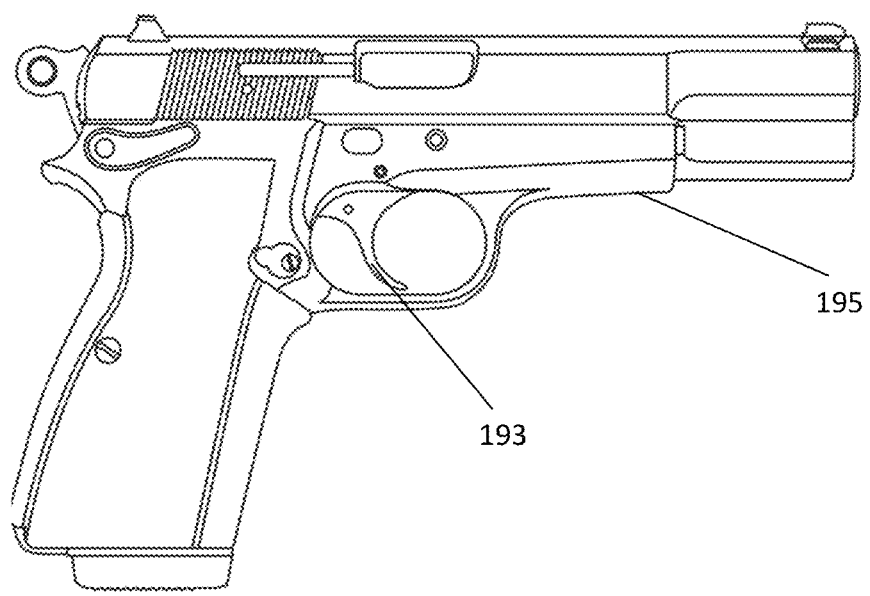
FIG. 1 is an illustration of an example firearm.

FIG. 1 is an illustration of an example firearm 190. The firearm includes a trigger 193 that when pulled back towards a rear of the firearm 190 causes the firearm 190 to fire or discharge. In the example shown, the firearm 190 is a hand gun. However, other types of firearms 190 may be used.

The firearm 190 further includes a rail 195. The rail 195 may allow a variety of accessories to be attached to the firearm 190 including lights, scopes, sights, etc. The rail 195 may be a standard rail such as a picatinny rail, weaver rail, or NATO rail. Any type of rail may be used.

Figure 2:
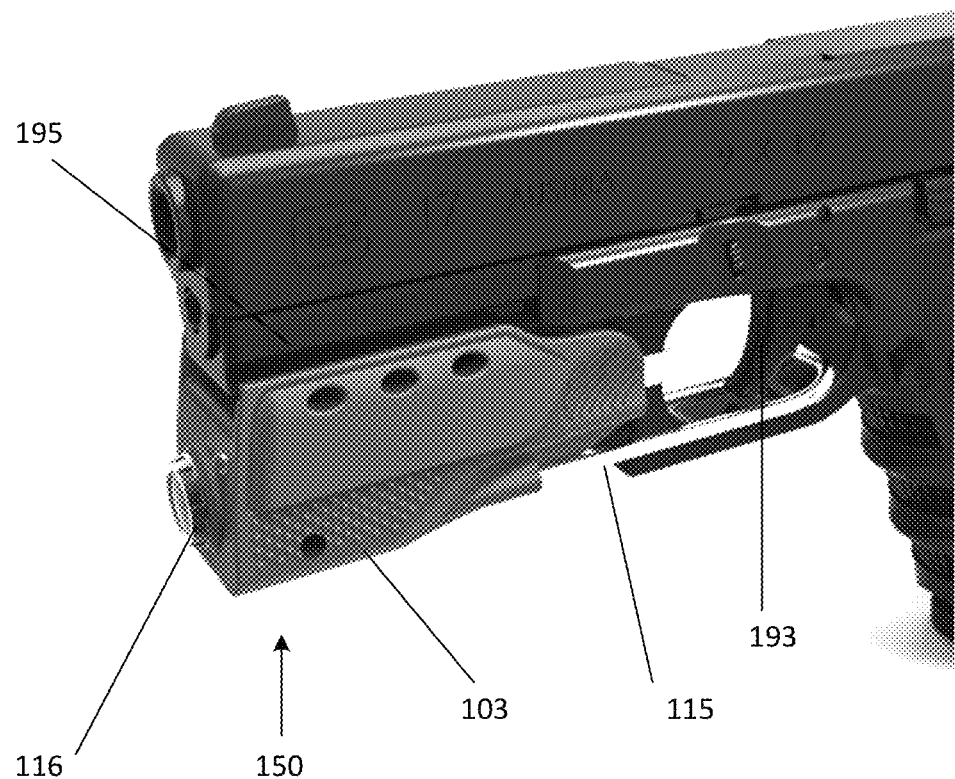
FIGS. 2 and 3 are illustrations of example firearms with attached safety modules.

FIG. 2 is an illustration of the example firearm 190 including a safety module 150. As shown, the safety module 150 includes a housing 103 that is adapted to couple with the rail 195 of the firearm 190. The housing 103 may be made from a variety of suitable materials including plastic and metal. Other materials may be used. The housing 103 may be removably attached to the firearm 190 thereby allowing the safety module 150 to be used with multiple firearms 190.

The safety module 150 further includes a trigger bar 115. As shown, the trigger bar 115 forms a loop that extends from the housing 103 and goes behind the trigger 193. As will be described further below, when in a first or locked state, the trigger bar 115 may be immobilized to prevent an operator of the firearm 190 from fully engaging the trigger 193 and firing the firearm 190. When in the second or unlocked state, the trigger bar 115 may be moveable to allow the operator of the firearm 190 to fully engage the trigger 193 and fire the firearm 190. The trigger bar 115 is designed to preclude or impede the rearward motion of the trigger. However, the trigger bar 115 does not block access to the trigger itself by the operator. Free access is always available for the operator to put their finger upon the trigger.

The safety module 150 may further include one or more sensors 116. In the example shown in FIG. 2, the sensor 116 is a camera. However, other types of sensors may be used.

The trigger bar 115 may be sized and shaped based on the particular make and model of the firearm 190. In particular, the trigger bar 115 may be sized and shaped based on the particular location of the rail 195 on the firearm 190 and the location of the trigger 193 on the firearm 190. The trigger bar 115 may be removeable from the safety module 150, allowing a user to use the safety module 150 with a variety of different firearms 190 by swapping out different trigger bars 115. Depending on the embodiment, trigger bars 115 may be manufactured for a variety of different firearm 190 makes and models.

Figure 3:
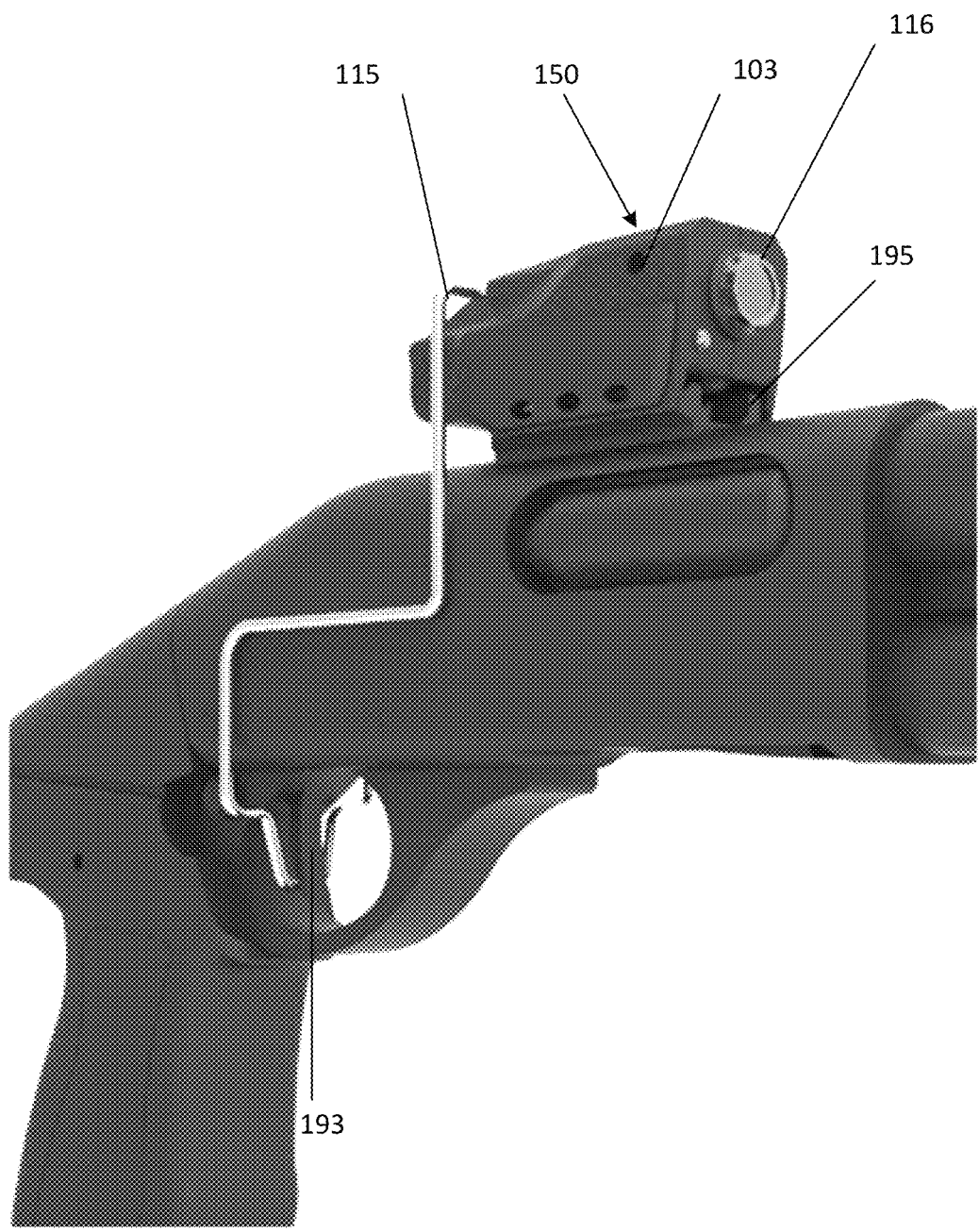

For example, continuing to FIG. 3, the safety module 150 is shown attached to a shotgun-type firearm 190. Unlike the handgun-type firearm 190 of FIG. 2, the shotgun-type firearm 190 has a rail 195 on the top of the firearm 190 and there is a larger distance between the rail 190 and the trigger 193. Accordingly, the trigger bar 115 has been lengthened and bent to accommodate the locations of the rail 195 and trigger 193.

Figure 4:
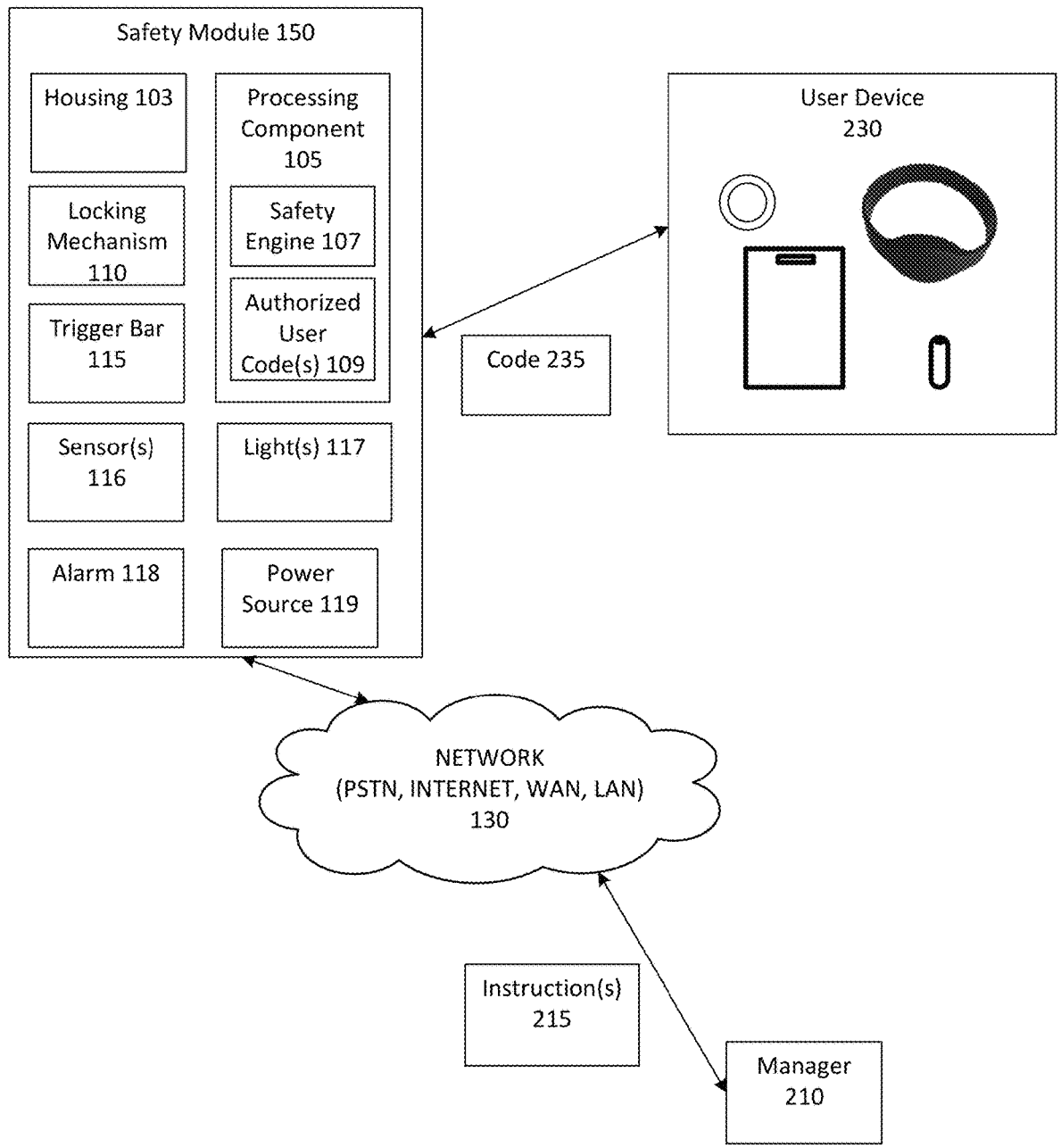
FIGS. 4-8 are illustrations of example methods for operating a safety module on a firearm.

FIG. 4 is an illustration of an environment 400 for using the safety module 150. As shown, the safety module 150 may include multiple components including, but not limited to, a housing 103, processing component 105, a locking mechanism 110, a trigger bar 115, one or more sensors 116, one or more lights 117, an alarm 118, and a power source 119.

The processing component 105 may include a processor and a memory and may be located within the housing. An example processing component may be some or all of the computing system 900 illustrated with respect to FIG. 9.

The processing component 105 may execute a safety engine 107. The safety engine 107 may transition the locking mechanism 110 between a first state and a second state. In the first state, the locking mechanism 110 may prevent the trigger bar 115 from moving and thereby prevent the trigger 193 of the firearm 190 from actuating. In the second state, the locking mechanism 110 may allow the trigger bar 115 to move and thereby allow the trigger 193 of the firearm 190 to be actuated. Depending on the embodiment, the locking mechanism 110 may be a solenoid, for example. Other types of locking mechanisms 110 may be used.

To determine when to transition from the first state and the second state, the processing component 105 may store one or more authorized user codes 109. Each authorized user code 109 may be a number that uniquely identifies a user of the firearm 190.

An operator of the firearm 190 may wear, carry, or hold what is referred to herein as a user device 230. As shown, example user devices 230 may include rings, bracelets, cards, and implantable devices. Other types of devices may be used such as glasses, googles, badges, gloves, watches, hats, helmets, etc.

Each user device 230 may include a wireless transmitter and may be configured to transmit a code 235 to the safety module 150 when the user device 230 is within range of the safety module 150. Depending on the embodiment, the user device 230 may include an RFID transmitter that may be energized and caused to transmit the code 235 when the RFID transmitter is within range of an RFID receiver associated with the safety module 150. Other wireless technologies may be used to transmit the code 235.

When the safety module 150 receives a code 235, the safety engine 107 may compare the received code 235 with one or more of the stored authorized user codes 109. If the received code 235 matches one of the authorized user codes 109 (indicating that an authorizer user is holding the firearm 190 or is in range of the firearm 190), the safety engine 107 may place or transition the locking mechanism 110 into the second state (i.e., the firing state).

As may be appreciated, to prevent an authorized user from giving the firearm 190 to an unauthorized user after placing the locking mechanism 110 in the second state, the safety engine 107 (while in the second state) may periodically receive the code 235 from the user device 230 and may redetermine whether the received code 235 matches an authorized user code 109. In the event that a received code 235 does not match an authorized user code 109, the safety engine 107 may place the locking mechanism 110 in the first state (i.e., the disabled or non-firing state). Furthermore, if a threshold amount of time passes and the safety engine 107 does not receive a code 235, the safety engine 107 may place the locking mechanism 110 in the first state.

The particular authorized user codes 109 stored by the safety engine 107 may be set by a user or administrator. In some embodiments, the authorized user codes 109 may be controlled by a manager 210. The manager 210 may be connected to the safety engine 107 via a network 130 such as the internet. The safety module 150 may include a networking component (e.g., WiFi, cellular, or other wireless technology) that allows it to periodically receive instructions 215 from the manager 210. The received instructions 215 may either add authorized user codes 109, remove authorized user codes 109, or indicate that no change has been made to the authorized user codes 109. The manager 210 may be a server, for example.

Depending on the embodiment, each instruction 215 may include all of the authorized user codes 109 for the safety module 150. Accordingly, when an instruction 215 is received by the safety module 150, the safety engine 107 may replace all of the stored authorized user codes 109 with the authorized user codes 109 included in the instruction 215.

In some embodiments, the manager 210 may provide an application, or API, through which a user can control the authorized user codes 109 associated with their safety module 150. For example, the user may register their safety module 150 with a user account or user profile associated with the manager 210. The user may then use the user account to specify what authorized user codes 109 should be associated with their safety module 150. The manager 210 may then provide an instruction 215 that includes the authorized user codes 109 to the safety module 150 through the network 130.

As may be appreciated, for the safety of the user and other users, it is important to ensure that the authorized user codes 109 used by the safety engine 107 are current and up-to-date. For example, if a user uses the manager 210 to remove an authorized user, it is very important that the corresponding authorized user code 109 is removed from the safety engine 107 as soon as possible.

Accordingly, in some embodiments, the safety engine 107 may maintain a record of the last time that the safety engine 107 received an instruction 215 from the manager 210. If the time is greater than a threshold time, the safety engine 107 may prevent the locking mechanism 110 from transitioning to the second state (i.e., the firing state) regardless of the received code 235. This may prevent a previously authorized nefarious user from stopping the safety module 150 from receiving an instruction 215 that might revoke their status as an authorized user. The threshold time may be one minute, ten minutes, fifteen minutes, etc.

The safety module 150 may further require that multiple authorized users be present when using the firearm 190. For example, a user being trained to use a firearm 190 may be required to have an instructor present while using the firearm 190. In such embodiments, the safety engine 107 may only allow the locking mechanism 110 to transition to the second state when a first code 235 is received from the user device 230 of the trainee and a second code 235 is received from the user device 230 of the trainer. This may ensure that the firearm 190 can only be fired by the trainee when the trainer is present. The safety module 150 may be configured for such operation by the manager 210. There is no limit to the number of codes 235 that may be required to operate the firearm 190.

Multiple codes 235 could also be useful in group firearm 190 scenarios. For example, members of a group may each have their own firearm 190. Each firearm 190 may include a safety module 150 that requires a first code 235 unique to the operator and a second code 235 that is associated with a leader of the group. The leader of the group could effectively disable all of the firearms 190 in the group by disabling or turning off their user device 230. Because the code 235 of the leader is no longer received by each of the safety modules 150 of the group members, each firearm 190 is prevented from being fired by its respective safety module 150. As may be appreciated, the above described scenario could be applicable to police or military training exercises where a commander or ranking officer desires to selectively allow or disallow their trainees from operating their firearms 190.

The safety module 150 may further include one or more sensors 116 that allow the safety module 150 to count the number of rounds that are fired by the firearm 190. For example, in one embodiment the safety module 150 may include an accelerometer that can be used to detect the recoil force caused by firing the firearm 190. In another example, the safety module 150 may include a sensor 116 that senses the movement of the trigger bar 115 caused by the operator pulling the trigger 193.

The safety module 150 may further use one or more sensors 116 to collect other data regarding the firearm 190. In one example, the sensors 116 may include a camera, and the safety module 150 may collect and store video data while the safety module 150 is in the second state (i.e., the firing state). In another example, the other data may include accelerometer data or position data that may indicate the position of the firearm 190 before and after the firearm 190 is fired. This data may be used to determine how the operator is holding the firearm 190 while firing.

The safety module 150 may further use the one or more sensors 116 to collect biometric data about the user. The biometric data may be used to determine a physiological state of the user such as a heart rate or a breathing rate.

Depending on the embodiment, some or all of the data collected by the sensors 116 may be provided by the safety engine 107 to the manager 210 through the network 130. The data may be stored by the manager 210 and associated with the user profile or user account associated with the safety module 150.

The safety module 150 may use the data collected by the various sensors 116 to provide additional safety features. For example, with respect to the number of rounds fired, the safety engine 107 may count the number of rounds that have been fired by the firearm 190 and may determine if a total allowed number of rounds has been exceeded or if a firing rate has been exceeded. If so, the safety engine 107 may temporality disable the firearm 190 by placing the locking mechanism 110 in the first state (i.e., the disabled or non-firing state).

The safety module 150 may further perform one or more safety functions based on the biometric data. For example, the safety engine 107 may determine that the user is acting erratically based on their heart rate or breathing rate and may determine to place the locking mechanism 110 in the first state (i.e., the disabled or non-firing state).

The safety module 150 may further use the collected data to critique or improve the performance of the operator of the firearm 190. For example, with respect to the video data collected by the safety engine 107, the safety engine 107 (or the manager 230) may process the video data to identify a likely target of each shot and the location where the shot ultimately lands. The difference between the target and the location may be determined by the safety engine 107 and may be used to determine an accuracy rate for the operator of the firearm 190. The determined accuracy rate may then be provided to the operator of the firearm 190.

Based on the determined accuracy rate, the safety engine 107 (or manager 230) may make recommendations to the operator of the firearm 190 to improve their accuracy. For example, based on data collected by the sensors 116 about how the operator is holding the firearm 190, the safety module 150 may recommend adjustments to the operator to improve their performance. The recommendations may be provided to the operator though an application or webpage associated with the manager 230, for example.

The safety module 150 may further provide real-time or near real time feedback to help improve the accuracy of the user. For example, to help train the operator to fire the firearm between heart beats, the safety engine 107 may use the biometric data to determine when the operator is between heart beats and may prompt the operator to fire based on the determination. The prompts may include turning on one or more lights 117 or providing haptic feedback, for example. Other prompts may be used.

In addition, the safety module 150 may transition the locking mechanism 110 between the first and second states based on the physiological state of the operator. For example, the safety module 150 may transition to the second state (i.e., the firing state) when the operator is between breaths, and may transition to the first state (i.e., the disabled state) when the operator is exhaling or inhaling.

The safety module 150 may convey certain information to the operator of the firearm 190 using the lights 117 and/or the alarm 118. For example, when the locking mechanism 110 is in the first state (i.e., the disabled state) the lights 117 may be red, and when the locking mechanism 110 is in the second state (i.e., the firing state) the lights 117 may be green. Similarly, when the locking mechanism 110 transitions to the first state from the second state, or when a code 235 is received that does not match an authorized user code 109, the alarm 118 may sound. The behavior of the lights 117 and/or the alarm 118 may be set by a user or administrator.

The safety module 150 may be powered by a power source 119. Depending on the embodiment, the power source 119 may be a rechargeable battery that may be charged using a variety of wired (e.g., USB) and wireless (e.g., Qi) methods. Depending on the embodiment, when the battery charge drops below a threshold charge, the safety module 150 and/or the manager 210 may alert the operator.

The manager 210, in addition to configuring authorized users 109, may provide a social networking functionality to users of the safety modules 150. For example, the manager 210 may allow users to create user profiles and share information such as video data collected by the safety module 150 from recent target shooting as well as calculated accuracy rates. Other functionality may be provided by the manager 210.

Figure 5:
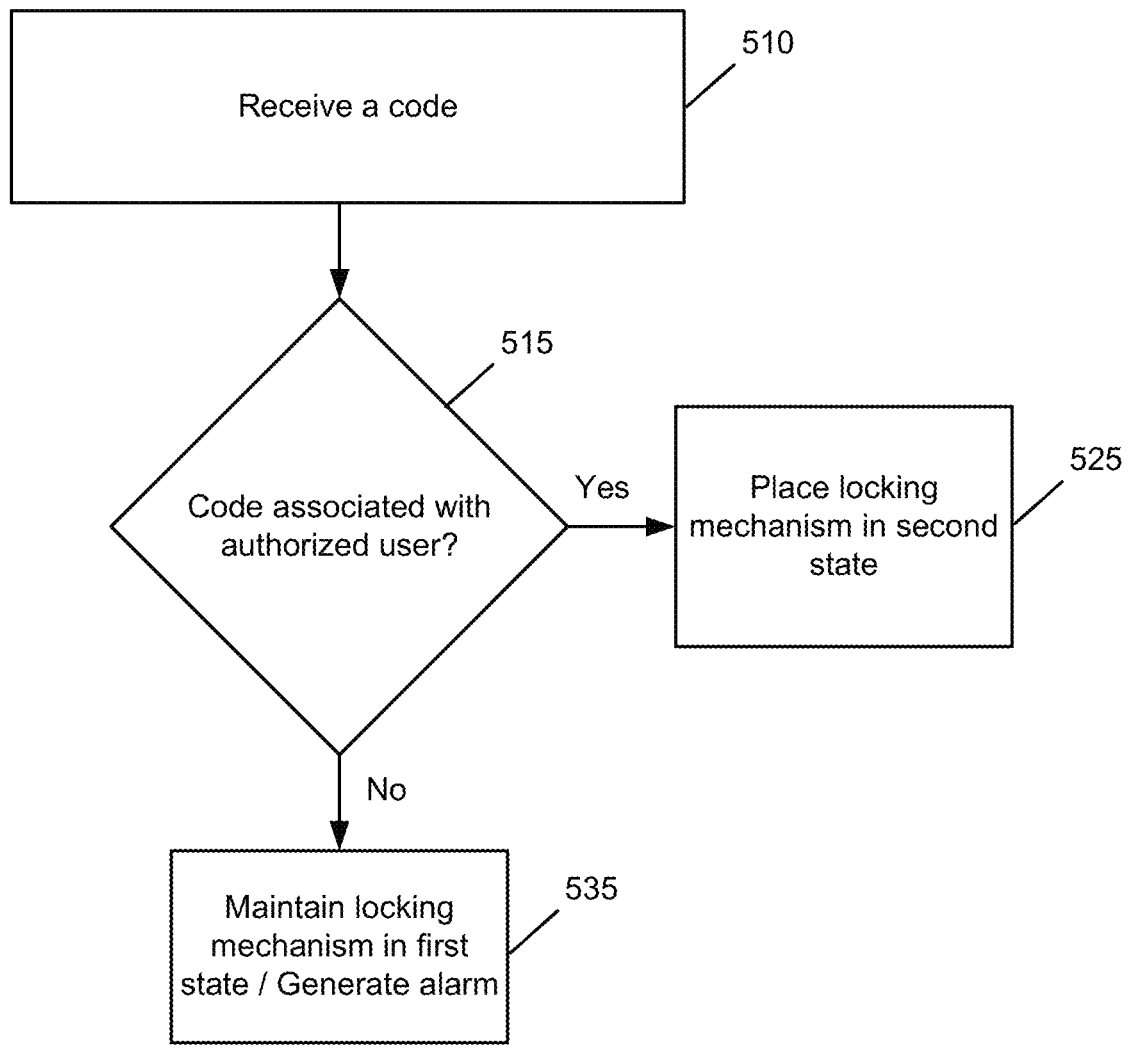

FIG. 5 is an illustration of an example method 500 for operating a safety module 150 on a firearm 190. The method 500 may be implemented by the safety engine 107 of the safety module 150.

At 510, a code is received. The code 235 may be received by the safety engine 107 from a user device 230. The code 235 may be an RFID code and the user device 230 may include an RFID chip and/or transmitter. Examples of user devices 230 include rings and bracelets. The safety engine 107 may be part of a safety module 150 that prevents an associated firearm 190 from firing by unauthorized users using a locking mechanism 110 and a trigger bar 115. The locking mechanism 110 may be in a first state where the locking mechanism 110 prevents the trigger bar 115 from moving. Because the trigger bar 115 extends behind a trigger 193 of the firearm 190, the firearm 190 cannot be fired while the locking mechanism 110 is in the first state.

At 515, a determination of whether the code is associated with an authorized user is made. The determination may be made by the safety engine 107 comparing the code 235 with one or more stored authorized user codes 109. If the code 235 matches any of the stored authorized user codes 109 then the method 500 may continue at 525. Else, the method 500 may continue at 535.

At 525, the locking mechanism is placed in a second state. The locking mechanism 110 may be placed in the second state by the safety engine 107 upon determining that the received code 235 is associated with an authorized user. While in the second state the trigger bar 115 is allowed to move by the locking mechanism 110. Accordingly, the trigger 193 of the firearm 190 is allowed to move, and the firearm 190 can be fired while the locking mechanism 110 is in the second state.

At 535, the locking mechanism remains in the first state. Because the code 235 did not match any of the authorized user codes 109, the safety engine 107 may keep the locking mechanism 110 in the first state thereby preventing the firearm 190 from firing. Depending on the embodiment, the safety engine 107 may sound an alarm 118 to indicate that an unauthorized user may be trying to use the firearm 190 and may send an indication of the unauthorized usage to the manager 210. The manager 210 may then notify one or more authorized users associated with the safety module 150.

Figure 6:
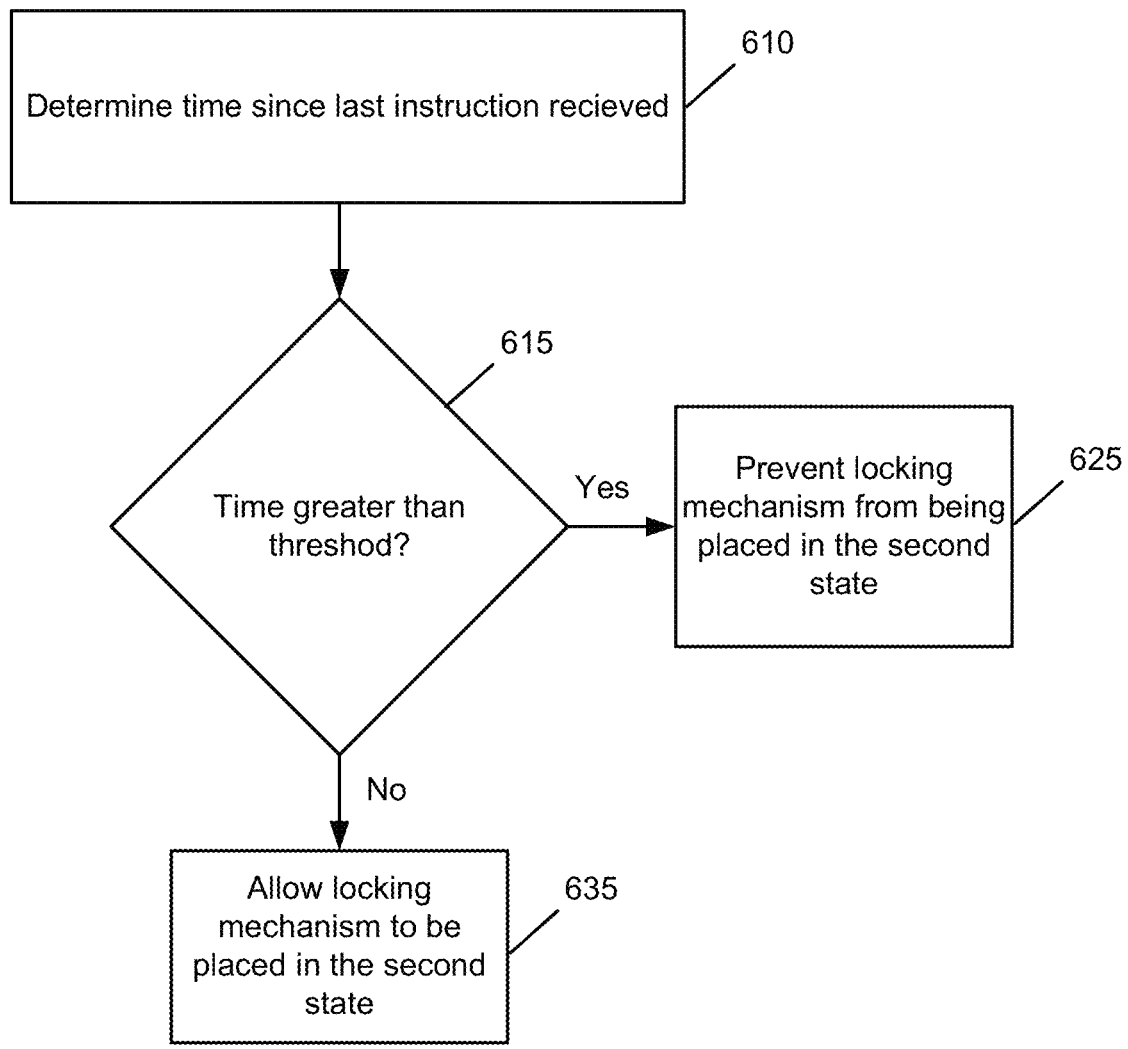

FIG. 6 is an illustration of an example method 600 for operating a safety module 150 on a firearm 190. The method 600 may be implemented by the safety engine 107 of the safety module 150.

At 610, a time since a last instruction was received is determined. The determination may be made by the safety engine 107 of the safety module 150. In some embodiments, the safety module 150 may periodically receive instructions 215 from a manager 210 through a network 130. The instructions 215 may be to add one or more authorized user codes 109, remove one or more authorized user codes 109, or to indicate that no changes have been made to the authorized user codes 109.

At 615, whether the time is greater than a threshold is determined. The determination may be made by the safety engine 107. The threshold may be set by a user or administrator. As may be appreciated, to ensure that any changes made to the authorized user codes 109 are adopted by the safety engine 107, the safety engine 107 may check whether instructions 215 are regularly being received from the manager 210. If the time is greater than the threshold, the method 600 may continue at 625. Else, the method 600 may continue at 635.

At 625, the locking mechanism is prevented from being placed in the second state. The locking mechanism 110 may be prevented from being placed in the second state by the safety engine 107. Because the time was greater than the threshold time, the safety engine 107 may assume that the stored authorized user codes 109 may not reflect any changes made by the manager 210 through the instructions 215. Accordingly, the safety engine 107 may prevent the locking mechanism 110 from being placed in the second state (i.e., the firing state) even when a code 235 that matches a stored authorized user code 109 is received. In some embodiments, the safety engine 107 may use the alarm 118 and/or lights 117 to indicate to the user that the locking mechanism 110 cannot be placed in the second state until an instruction 215 is received.

At 635, the locking mechanism is allowed to be placed in the second state. The locking mechanism 110 may be allowed to be placed in the second state by the safety engine 107. Because the time was less than the threshold time, in the event that a code 235 that matches an authorized user code 109 is received, the locking mechanism 110 may be placed in the second state by the safety engine 107.

Figure 7:
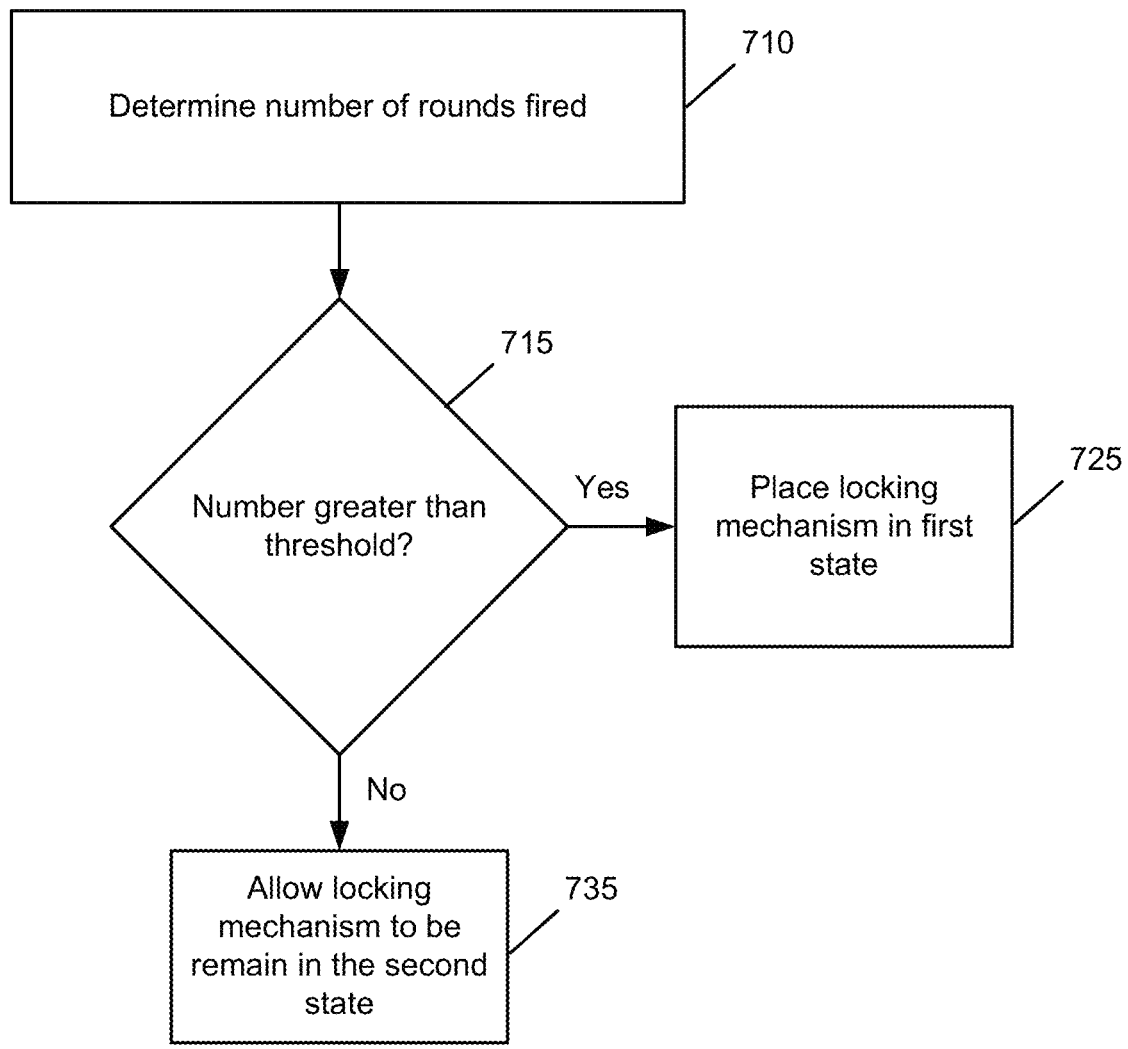

FIG. 7 is an illustration of an example method 700 for operating a safety module 150 on a firearm 190. The method 700 may be implemented by the safety engine 107 of the safety module 150.

At 710, a number of rounds fired is determined. The determination may be made by the safety engine 107 of the safety module 150. In some embodiments, the safety engine 107 may keep track of the number of rounds that have been fired by the firearm 190 that the safety module 150 is attached to. The safety engine 107 may determine the number of rounds based on movement of the trigger bar 115 or based on data received from one or more sensors 116 such as an accelerometer.

At 715, whether the number of rounds fired is greater than a threshold is determined. The determination may be made by the safety engine 107. The threshold may be set by a user or administrator and may be received from the manager 210. For example, as a safety precaution, the number of rounds that may be fired by the firearm 190 may be limited. Alternatively, rather than a threshold number of rounds, the safety module 150 may enforce a firing rate. If the number (or rate) is greater than the threshold, the method 700 may continue at 725. Else, the method 700 may continue at 735.

At 725, the locking mechanism is placed in the first state. The locking mechanism 110 may be placed in the first state by the safety engine 107. As described above, the firearm 190 cannot be fired while in the first state. Depending on the embodiment, the locking mechanism 110 may return to the second state after some amount of time has elapsed since the locking mechanism 110 was placed in the first state (i.e., cooling-off period).

At 735, the locking mechanism is allowed to be placed in the second state. The locking mechanism 110 may be allowed to be placed in the second state by the safety engine 107.

Figure 8:
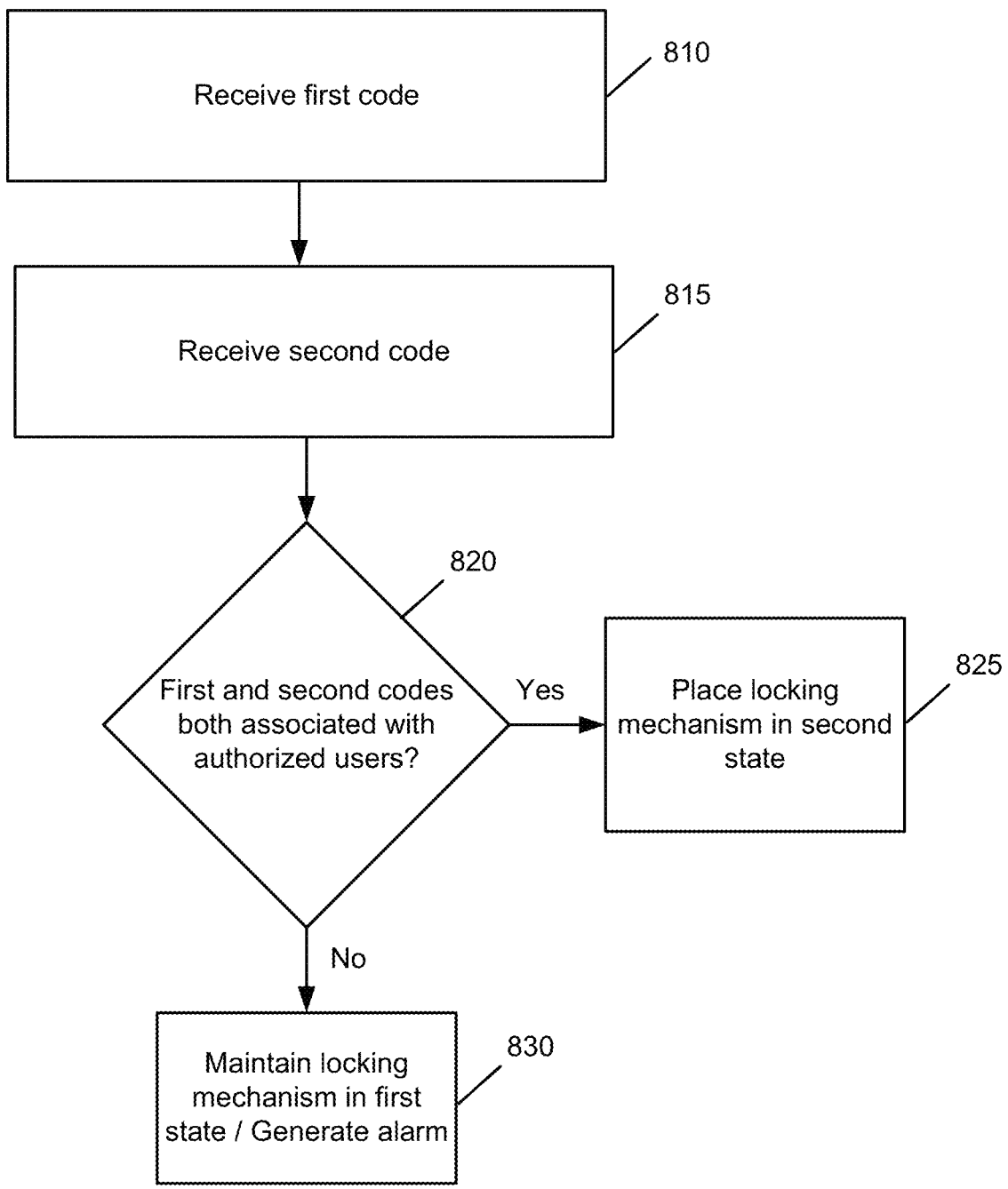

FIG. 8 is an illustration of an example method 800 for operating a safety module 150 on a firearm 190. The method 800 may be implemented by the safety engine 107 of the safety module 150.

At 810, a first code is received. The first code 235 may be received by the safety engine 107 of the safety module 150 from a user device 230 associated with a first user. The first user may be an operator of the firearm 190 associated with the safety module 150. The first user may be holding the firearm 190. The first code 235 may be received from an RFID chip associated with the user device 230.

At 815, a second code is received. The second code 235 may be received by the safety engine 107 of the safety module 150 from a user device 230 associated with a second user. The second user may be a supervisor of the first user. For example, the second user may be an instructor who is required to be present when the first user is operating the firearm 190. The second user may not be holding the firearm 190 but may be near enough to the firearm 190 that the safety engine 107 receives the second code 235.

At 820, whether both the first code and the second code are associated with authorized users is determined. The determination may be made by the safety engine 107. If both codes 235 are associated with authorized users the method 800 may continue at 825. Else, the method 800 may continue at 830.

At 825, the locking mechanism is placed in a second state. The locking mechanism 110 may be placed in the second state by the safety engine 107 upon determining that both the received first code 235 and the received second code 235 are associated with authorized users. The firearm 190 may be fired by the first user while the locking mechanism 110 is in the second state.

At 830, the locking mechanism remains in the first state. Because one or both of the first code 235 and the second code 235 did not match any of the authorized user codes 109, the safety engine 107 may keep the locking mechanism 110 in the first state thereby preventing the firearm 190 from firing.

Figure 9:
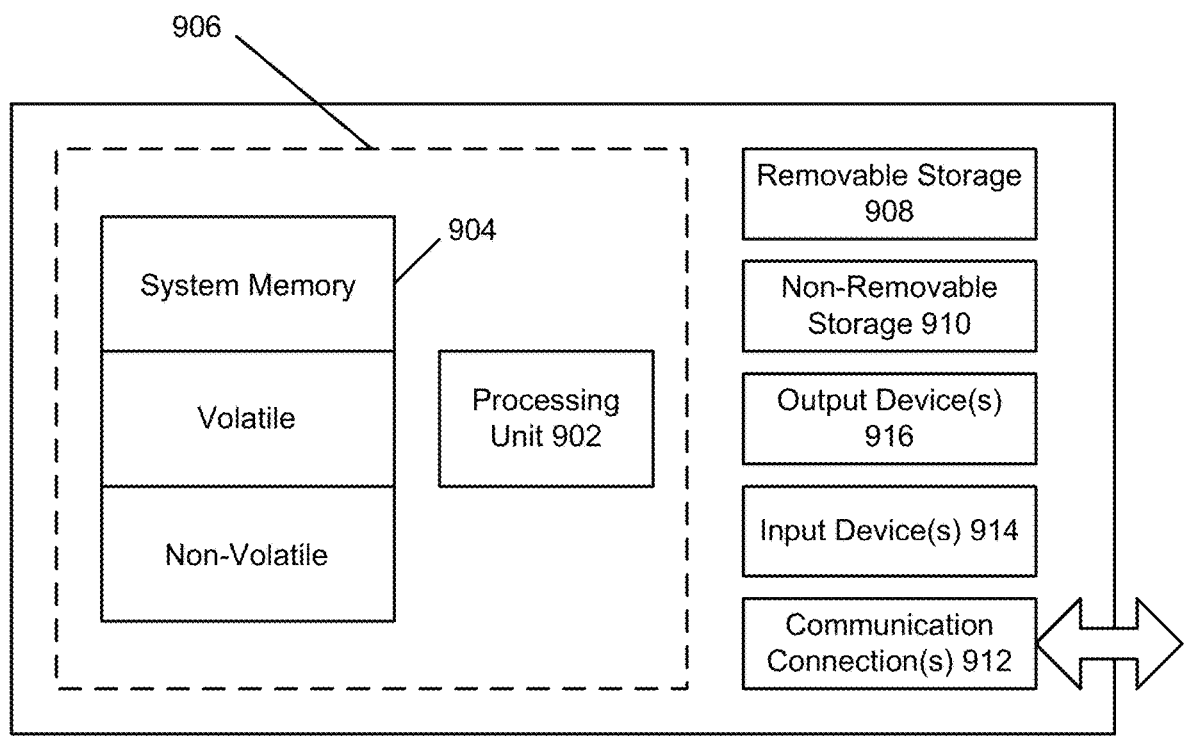
FIG. 9 illustrates an example computing device.

FIG. 9 shows an exemplary computing environment in which example embodiments and aspects may be implemented. The computing system environment is only one example of a suitable computing environment and is not intended to suggest any limitation as to the scope of use or functionality.

Numerous other general purpose or special purpose computing system environments or configurations may be used. Examples of well-known computing systems, environments, and/or configurations that may be suitable for use include, but are not limited to, personal computers, servers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 9, an exemplary system for implementing aspects described herein includes a computing device, such as computing device 900. In its most basic configuration, computing device 900 typically includes at least one processing unit 902 and memory 904. Depending on the exact configuration and type of computing device, memory 904 may be volatile (such as random access memory (RAM)), non-volatile (such as read-only memory (ROM), flash memory, etc.), or some combination of the two. This most basic configuration is illustrated in FIG. 9 by dashed line 906.

Computing device 900 may have additional features/functionality. For example, computing device 900 may include additional storage (removable and/or non-removable) including, but not limited to, magnetic or optical disks or tape. Such additional storage is illustrated in FIG. 9 by removable storage 908 and non-removable storage 910.

Computing device 900 typically includes a variety of tangible computer readable media. Computer readable media can be any available tangible media that can be accessed by device 900 and includes both volatile and non-volatile media, removable and non-removable media.

Tangible computer storage media include volatile and non-volatile, and removable and non-removable media implemented in any method or technology for storage of information such as computer readable instructions, data structures, program modules or other data. Memory 904, removable storage 908, and non-removable storage 910 are all examples of computer storage media. Tangible computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 900. Any such computer storage media may be part of computing device 900.

Computing device 900 may contain communications connection(s) 912 that allow the device to communicate with other devices. Computing device 900 may also have input device(s) 914 such as a keyboard, mouse, pen, voice input device, touch input device, etc. Output device(s) 916 such as a display, speakers, printer, etc. may also be included. All these devices are well known in the art and need not be discussed at length here.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system for preventing the unauthorized use of a firearm comprising:
    a housing that is removably attached to a rail of a firearm;
    a locking mechanism within the housing;
    a trigger bar that is connected to the locking mechanism and that extends from the locking mechanism on the rail of the firearm to behind a trigger of the firearm when the housing is attached to the firearm; and
    a processing component that is configured to place the locking mechanism in one of a first state or a second state, wherein in the first state the locking mechanism prevents the trigger bar from moving such that a normal movement of the trigger is impeded and in the second state the locking mechanism allows the trigger bar to move such that the normal movement of the trigger is unimpeded.

2. The system of claim 1, wherein the processing component is further configured to:
    wirelessly receive a code;
    determine if the received code is associated with an authorized user; and
    when it is determined that the received code is associated with an authorized user, place the locking mechanism in the second state.

3. The system of claim 1, wherein the processing component is further configured to:
    wirelessly receive a code;
    determine if the received code is associated with an authorized user; and
    when it is determined that the received code is not associated with an authorized user, place the locking mechanism in the first state.

4. The system of claim 3, wherein determining if the received code is associated with an authorized user comprises the processing component:
    accessing one or more authorized user codes stored by the processing component in a memory; and
    determining if the received code matches any of the one or more authorized user codes.

5. The system of claim 4, wherein the processing component is further configured to:
    receive an instruction related to the one or more authorized user codes; and update the one or more authorized user codes in response to the received instruction.

6. The method of claim 5, wherein the instruction is one or more of an instruction to add an authorized user code to the one or more authorized user codes, an instruction to remove an authorized user code from the one or more authorized user codes, and an instruction to make no changes to the one or more authorized user codes.

7. The system of claim 5, wherein the processing component is further configured to:
   determine that a threshold amount of time has passed since an instruction related to the one or more authorized user codes has been received; and
   in response to the determination, prevent the locking mechanism from being placed in the second state.

8. The system of claim 1, wherein the processing component is further configured to:
   while in the second state:
      determine that a threshold amount of time has passed since a code has been received; and
      in response to the determination, place the locking mechanism in the first state.

9. The system of claim 1, wherein the system further comprises one or more sensors within the housing, wherein the one or more sensors are configured to collect data about the firearm and an operator of the firearm, and the processing component is further configured to transmit the collected data to a server.

10. The system of claim 1, wherein the system further comprises a camera within the housing, and the processor is further configured to:
    while in the second state, receive and store video data from the camera.

11. The system of claim 10, wherein the processing component is further configured to:
    process the stored video data to determine an accuracy for an operator of the firearm.

12. The system of claim 1, wherein the processing component is further configured to:
    while in the second state:
       determine a number of rounds fired by the firearm;
       determine that the number of rounds exceeds a threshold number of rounds; and
       in response to the determination, place the locking mechanism in the first state.

13. The system of claim 12, wherein the processing component is further configured to determine the number of rounds using an accelerometer.

14. The system of claim 1, wherein the processing component is further configured to:
    wirelessly receive a first code and a second code;
    determine that the received first code and the received second code are both associated with an authorized user of a plurality of authorized users; and
    in response to the determination, place the locking mechanism in the second state.

15. The system of claim 14, wherein the first code is associated with an operator of the firearm and the second code is received from a non-operator of the firearm.

16. The system of claim 1, wherein the processing component is further configured to:
    determine a physiological state of an operator of the firearm; and
    based on the determined physiological state, place the locking mechanism in the first state or the second state.

17. The system of claim 16, wherein the processing component is further configured to:
    provide haptic feedback based on the physiological state of the operator of the firearm.

18. The system of claim 1, wherein the housing remains attached to the firearm while the locking mechanism is in the second state and the locking mechanism allows an operator to put their finger on the trigger while the locking mechanism in the first state.

19. A system for preventing the unauthorized use of a firearm comprising:
    a housing that is removably attached to an exterior of a firearm;
    a locking mechanism within the housing;
    a trigger bar that is connected to the locking mechanism and that extends from the locking mechanism to a trigger of the firearm when the housing is attached to the firearm; and
    a processing component that is configured to place the locking mechanism in one of a first state or a second state, wherein in the first state the locking mechanism allows an operator to put their finger on the trigger but prevents the trigger bar from moving such that a normal movement of the trigger is impeded and in the second state the locking mechanism allows the trigger bar to move such that the normal movement of the trigger is unimpeded.

20. A system for preventing the unauthorized use of a firearm comprising:
    a housing that is removably attached to an exterior of a firearm;
    a locking mechanism within the housing;
    a trigger bar that is connected to the locking mechanism and that extends from the locking mechanism to a trigger of the firearm when the housing is attached to the firearm; and
    a processing component that is configured to place the locking mechanism in one of a first state or a second state, wherein in the first state the locking mechanism prevents the trigger bar from moving such that a normal movement of the trigger is impeded and in the second state the locking mechanism allows the trigger bar to move such that the normal movement of the trigger is unimpeded, wherein the housing remains attached to the firearm while the locking mechanism is in the second state.

* * * * *